(12) United States Patent
Okoniewski

(10) Patent No.: US 9,011,324 B2
(45) Date of Patent: Apr. 21, 2015

(54) ACCESS ASSEMBLY INCLUDING ONE OR MORE FOLDABLE CAPS

(75) Inventor: Gregory Okoniewski, North Haven, CT (US)

(73) Assignee: Covidien LP, Mansfield, MA (US)

( * ) Notice: Subject to any disclaimer, the term of this patent is extended or adjusted under 35 U.S.C. 154(b) by 393 days.

(21) Appl. No.: 13/223,330

(22) Filed: Sep. 1, 2011

(65) Prior Publication Data

US 2012/0130188 A1     May 24, 2012

Related U.S. Application Data

(60) Provisional application No. 61/416,769, filed on Nov. 24, 2010.

(51) Int. Cl.
    *A61B 1/32*     (2006.01)
    *A61B 17/34*     (2006.01)

(52) U.S. Cl.
    CPC ..... *A61B 17/3423* (2013.01); *A61B 2017/3443* (2013.01); *A61B 2017/3466* (2013.01)

(58) Field of Classification Search
    CPC .................. A61B 17/3423; A61B 2017/3466; A61B 2017/3443; A61B 1/32
    USPC ........... 600/184, 208, 205–207; 606/191, 185
    See application file for complete search history.

(56) References Cited

U.S. PATENT DOCUMENTS

| | | | |
|---|---|---|---|
| 2004/0054353 A1* | 3/2004 | Taylor | 606/1 |
| 2006/0247673 A1 | 11/2006 | Voegele et al. | |
| 2008/0051739 A1* | 2/2008 | McFarlane | 604/278 |
| 2008/0257918 A1* | 10/2008 | Vogel et al. | 222/480 |
| 2009/0118587 A1 | 5/2009 | Voegele et al. | |
| 2009/0187079 A1 | 7/2009 | Albrecht et al. | |
| 2010/0081871 A1* | 4/2010 | Widenhouse et al. | 600/104 |
| 2010/0081882 A1 | 4/2010 | Hess et al. | |
| 2010/0094227 A1 | 4/2010 | Albrecht et al. | |
| 2010/0228198 A1 | 9/2010 | Widenhouse et al. | |
| 2010/0240960 A1 | 9/2010 | Richard | |
| 2010/0249516 A1 | 9/2010 | Shelton, IV et al. | |
| 2010/0249526 A1 | 9/2010 | Shelton, IV et al. | |
| 2010/0268035 A1 | 10/2010 | Oberlander et al. | |

FOREIGN PATENT DOCUMENTS

| | | |
|---|---|---|
| EP | 0673626 A1 | 9/1995 |
| EP | 2044889 A1 | 4/2009 |
| EP | 2090259 A1 | 8/2009 |
| EP | 2168511 A2 | 3/2010 |
| EP | 2305151 A1 | 4/2011 |

OTHER PUBLICATIONS

European Search Report for corresponding EP11250791 date of mailing is Apr. 5, 2012 (5 pgs).

\* cited by examiner

*Primary Examiner* — Tuan V Nguyen
*Assistant Examiner* — Tin Nguyen

(57) ABSTRACT

An access assembly is provided including a tubular member having a proximal end and a distal end, the proximal end in mechanical cooperation with a foldable cap member having a first set of lumens extending the length of the tubular member. The access assembly also includes a first ring secured at the proximal end of the tubular member and a second ring secured at the distal end of the tubular member. The foldable cap member is configured to fold in at least one direction to expose a second set of lumens extending the length of the tubular member.

11 Claims, 5 Drawing Sheets

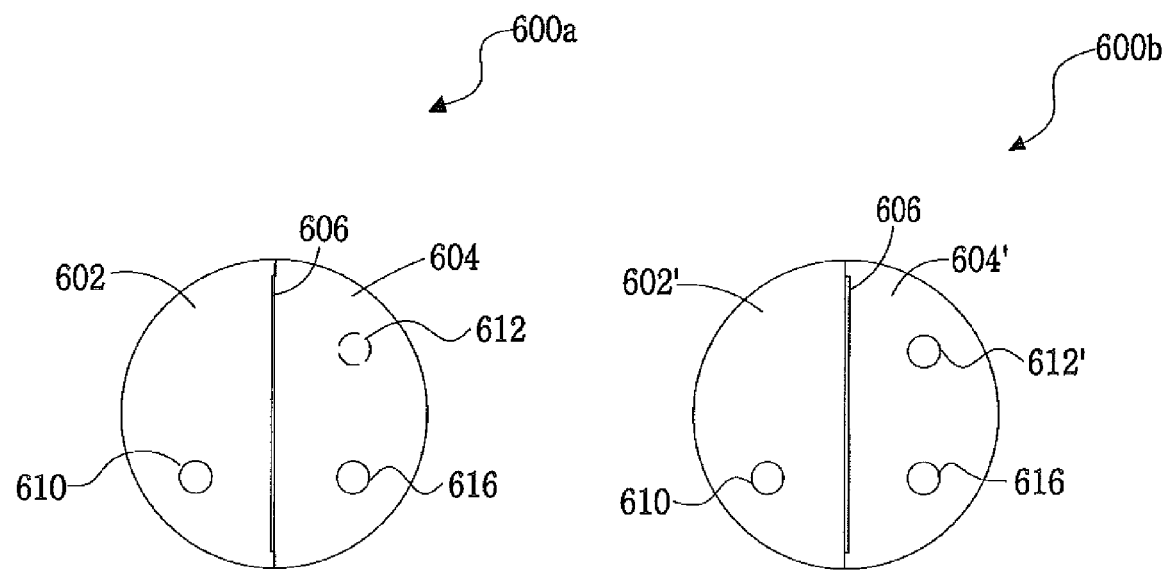
Fig. 6a
Fig. 6b
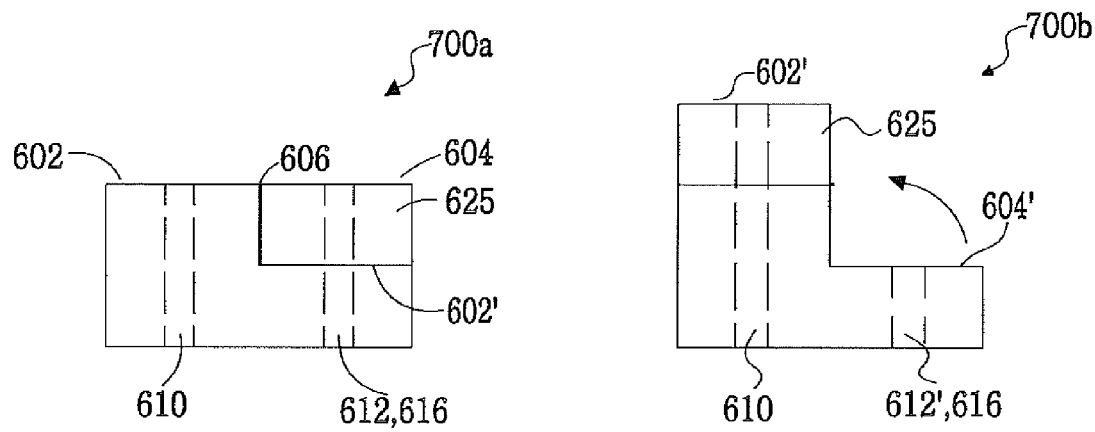
Fig. 7a
Fig. 7b

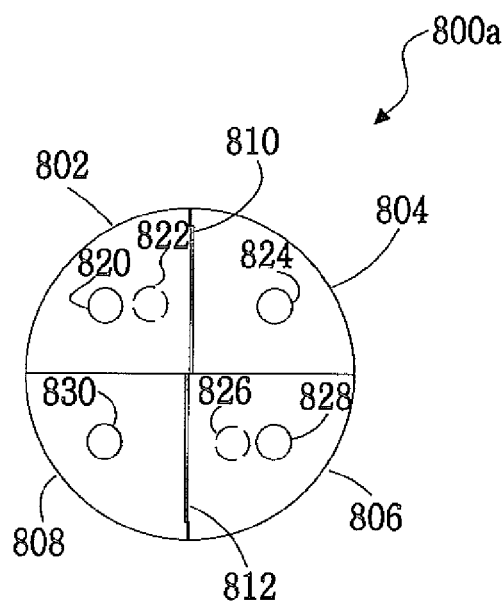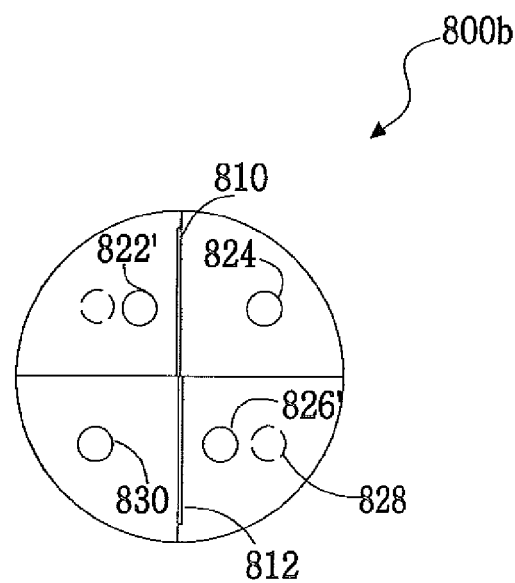
Fig. 8a　　　　　　　　　　Fig. 8b
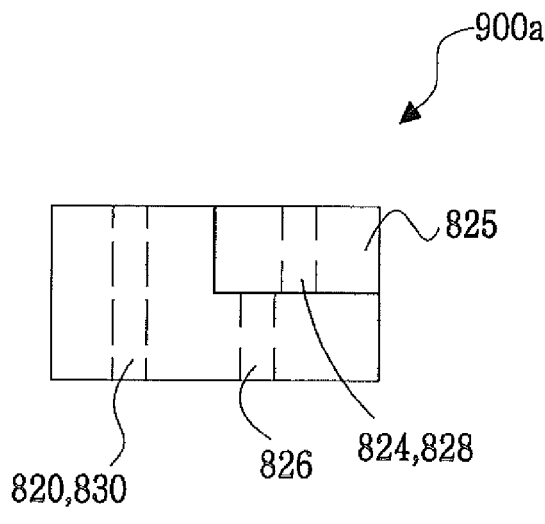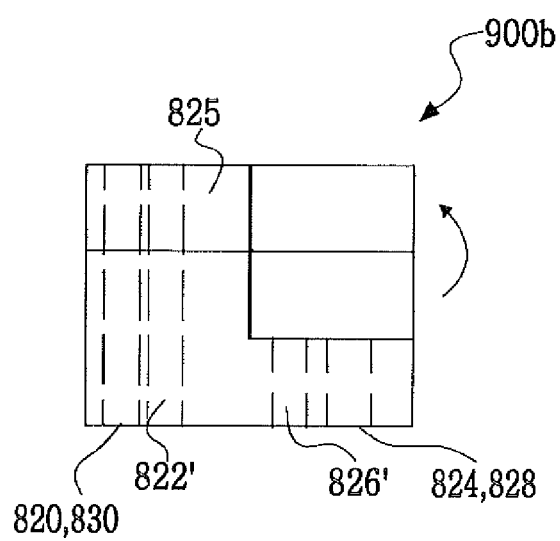
Fig. 9a　　　　　　　　　　Fig. 9b

ACCESS ASSEMBLY INCLUDING ONE OR MORE FOLDABLE CAPS

CROSS REFERENCE TO RELATED APPLICATIONS

The present application claims the benefit of and priority to U.S. Provisional Patent Application Ser. No. 61/416,769 filed on Nov. 24, 2010, the entire contents of which are incorporated herein by reference.

BACKGROUND

1. Technical Field

The present disclosure relates to an apparatus and method for accessing a body cavity. More particularly, the present disclosure relates to an access assembly including one or more foldable caps.

2. Background of Related Art

Access assemblies configured for reception through an incision into an abdominal cavity are known, as are methods of inserting the access assemblies therethrough. Traditional access assemblies include a rigid cannula that is received through the tissue of the body wall into the body cavity. Endoscopic, laparoscopic and other suitable instruments may then be directed through a housing on the proximal end of the cannula to access the body cavity in a sealing manner in a variety of electrosurgical procedures.

Moreover, compressible assemblies configured for accessing a body cavity and permitting reception of electrosurgical instruments therethrough in a sealing manner are also known. Such compressible assemblies are composed of silicone, thermoplastic elastomers (TPE), rubber, foam, gel and other compressible materials and are configured to be compressed to facilitate insertion into an incision. Typically, such assemblies are deformed by a surgeon using his/her fingers or with the assistance of a grasping device, e.g., forceps. Compression of the assembly reduces the profile of the assembly, thereby facilitating reception of the assembly into the incision. Upon release of the compressive force, the compressed assembly returns to an uncompressed configuration. In the uncompressed configuration, the access assembly seals the incision into the body cavity. The assembly may have one or more access ports for receiving the electrosurgical instruments therethrough and applying electrosurgical energy to tissue.

Therefore, it would be beneficial to have an access assembly configured to be inserted through tissue, such that surgical instruments may be easily inserted therethrough. It would also be beneficial to have an access assembly that is reconfigurable to accommodate a different number of surgical instruments.

SUMMARY

Accordingly, an improved access assembly is provided. The access assembly includes a tubular member having a proximal end and a distal end, the proximal end in mechanical cooperation with a foldable cap member having a first set of lumens extending the length of the tubular member. The access assembly also includes a first ring secured at the proximal end of the tubular member and a second ring secured at the distal end of the tubular member. The foldable cap member is configured to fold in at least one direction to expose a second set of lumens extending the length of the tubular member.

The first ring is configured to be received external of the tissue, whereas the second ring is configured to be received within a body cavity. The tubular member is configured to be tapered in a first position to facilitate insertion through the tissue and is configured to define a substantially hour-glass shape in a second position.

In another exemplary embodiment, the foldable cap member includes two equally sized portions pivotable attached to each other. The first portion is configured to snap fit over the second portion to expose the second set of lumens. In yet another exemplary embodiment, the foldable cap member includes a plurality of segments or portions pivotably attached to each other.

The first set of lumens are configured to be a first size and the second set of lumens are configured to be a second size, the first and second sizes being different from each other. In another exemplary embodiment, the second sets of lumens are configured to be slit sealing members.

Also provided is a method of accessing a body cavity. The method includes the steps of providing a tubular member having a proximal end and a distal end, the proximal end in mechanical cooperation with a foldable cap member having a first set of lumens extending the length of the tubular member; providing a first ring secured at the proximal end of the tubular member; and providing a second ring secured at the distal end of the tubular member; wherein the foldable cap member is configured to fold in at least one direction to expose a second set of lumens extending the length of the tubular member.

In addition, while certain aspects of this disclosure are described as relating to laparoscopic surgery via the abdominal wall, it should be understood that the present invention is equally relevant to, and may be employed in connection with, other types of surgery such as incision-less surgery, whereby access to a body cavity is provided via a natural orifice such as the vagina, anus, mouth, ear, nasal passage, etc.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein;

FIG. 6A is a top view of a cap assembly, according to an aspect of the present disclosure, where two channels are visible or accessible by the surgeon;

FIG. 6B is a top view of the cap assembly of FIG. 6A, according to an aspect of the present disclosure, where the foldable cap has been folded such that three channels are visible or accessible by the surgeon;

FIG. 7A is a side view of the foldable cap of FIG. 6A, according to an aspect of the present disclosure, depicting the foldable cap in a first configuration;

FIG. 7B is a side view of the foldable cap of FIG. 6B, according to an aspect of the present disclosure, depicting the foldable cap in a second configuration;

FIG. 8A is a top view of a cap assembly, according to an aspect of the present disclosure, where four channels are visible or accessible by the surgeon;

FIG. 8B is a top view of the cap assembly of FIG. 8A, according to an aspect of the present disclosure, where the foldable cap has been folded such that six channels are visible or accessible by the surgeon;

FIG. 9A is a side view of the foldable cap of FIG. 8A, according to an aspect of the present disclosure, depicting the foldable cap in a first configuration; and FIG. 9B is a side view of the foldable cap of FIG. 8B, according to an aspect of the present disclosure, depicting the foldable cap in a second configuration.

DETAILED DESCRIPTION

Figure 1:
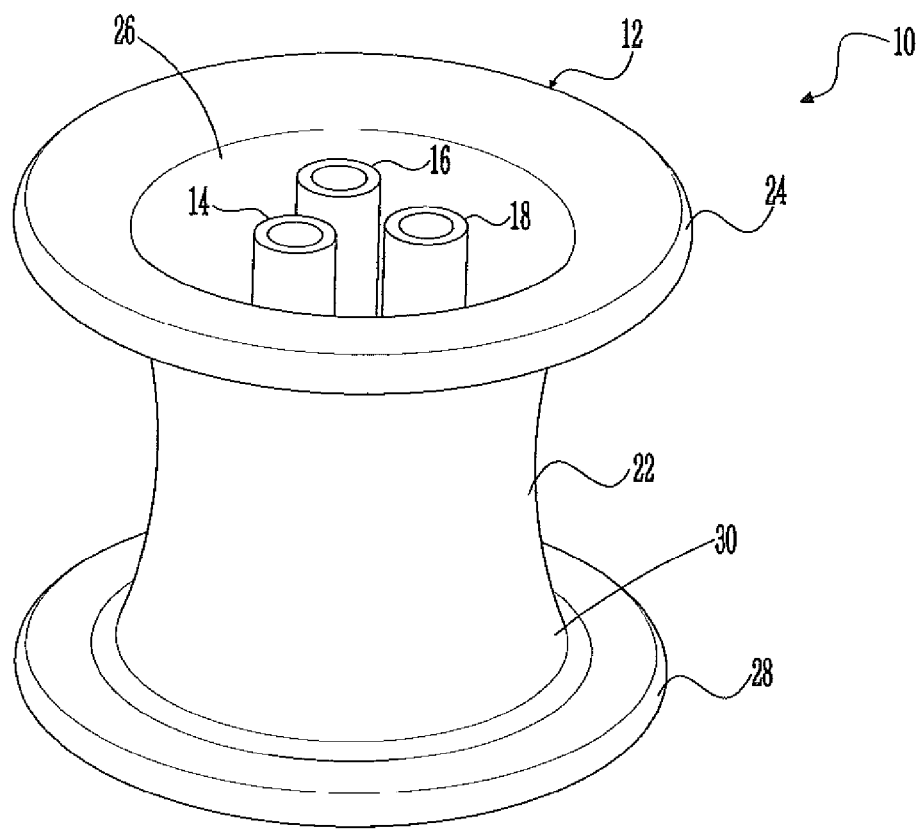
FIG. 1 is a perspective view of an access assembly having a plurality of channels.

The access ports of the present disclosure, either alone or in combination with a cannula assembly, provide a substantially fluid-tight seal between a body cavity of a patient and the outside atmosphere. The access ports, or seal assemblies, of the present disclosure are configured to receive surgical instruments of varying diameter. Various surgical procedures contemplated include laparoscopic and arthroscopic surgical procedures.

The access ports of the present disclosure contemplate the introduction of various types of instrumentation adapted for insertion through a trocar and/or cannula assembly while maintaining a substantially fluid-tight interface about the instrument to help preserve the atmospheric integrity of a surgical procedure from gas and/or fluid leakage. Examples of instrumentation include, but are not limited to, clip appliers, graspers, dissectors, retractors, staplers, laser probes, photographic devices, endoscopes and laparoscopes, tubes, and the like. Such instruments will collectively be referred to as "instruments" or "instrumentation."

Embodiments of the presently disclosed apparatus will now be described in detail with reference to the drawings, in which like reference numerals designate identical or corresponding elements in each of the several views. As used herein, the term "distal" refers to that portion of the tool, or component thereof which is further from the user while the term "proximal" refers to that portion of the tool or component thereof which is closer to the user. While the use of the access assembly is often described herein as engaging an incision, it should be recognized that this is merely exemplary and is not intended to limit the use of the assembly in any way, but rather it should be recognized that the present disclosure is intended to be useable in all instances in situations in which the access assembly engages an incision, a naturally occurring orifice, or any other suitable opening. The port is usable through an incision or through a naturally occurring orifice.

Figure 2:
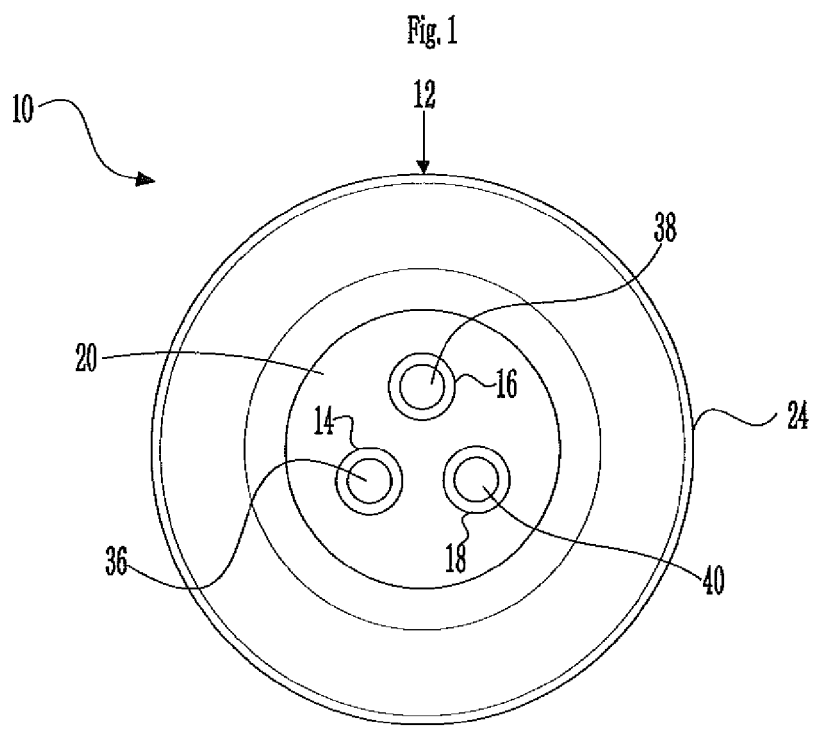
FIG. 2 is a top view of the access assembly of FIG. 1 illustrating the plurality of channels.
Figure 3:
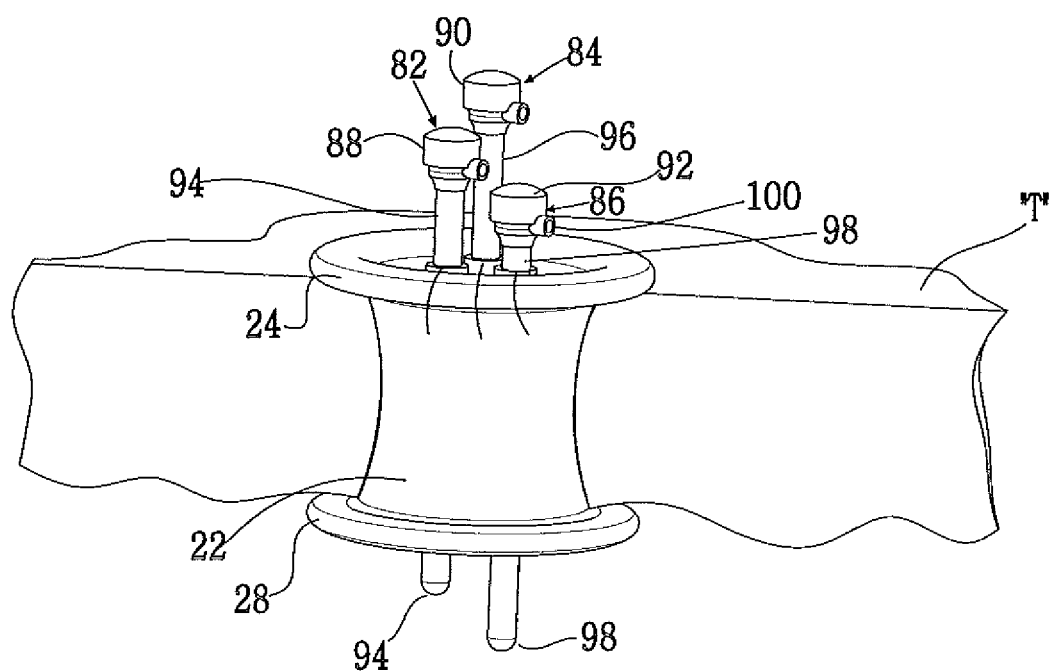
FIG. 3 is a perspective view of the access assembly of FIG. 1 inserted through tissue during a surgical procedure.

Referring to FIGS. 1-3, there is disclosed a flexible port seal 10 for use in single incision surgery. Flexible port seal 10 is flexible or compressible to allow it to be inserted through a single incision in the body of a patient such that after insertion it will expand and seal within the incision. Additionally, the flexible nature of flexible port seal 10 allows surgical instruments inserted therethrough to be manipulated relative to their respective axes and thus allows a relatively high degree of movement of the surgical instruments to orient them appropriate to the tissue being operated upon.

Flexible port seal 10 generally includes an outer tissue seal 12 having one or more throughports 14, 16, and 18 extending therethrough. Throughports 14, 16, and 18 are provided to receive various surgical cannulas and/or instruments through openings 36, 38, 40, respectively. The close proximity of throughports 14, 16, and 18 allows for unrestricted, independent movement of the surgical instruments inserted therethrough.

Outer tissue seal 12 is formed from a flexible material which, as noted hereinabove, allows flexible port seal 10 to be compressed and inserted through an incision in the body of a patient as well as allowing for independent movement of throughports 14, 16, and 18. Outer tissue seal 12 may be formed of various materials such as, for example, silicone, thermoplastic elastomers, rubber, foam, gel, etc. Where desired, throughports 14, 16, and 18 may also be formed from various flexible materials and may be integrally formed therewith.

With continued reference to FIGS. 1-3, outer tissue seal 12 includes a central portion 22 having an upper rim 24 located at a proximal end 26 of central portion 22. A lower rim 28 is located on a distal end 30 of central portion 22. Upper rim 24 and lower rim 28 aid in preventing movement of flexible port seal 10 longitudinally through the incision in the patient.

It should be recognized that throughports 14, 16, and 18 may have different lengths or diameters as compared to each other, and may respectively extend in either direction for any distance relative to the central portion 22. For example, any one or more of the throughports 14, 16, 18 may extend beyond the distal end 30 of central portion 22 or may extend to less than the proximal end 26 of the central portion 22. These differences in lengths may allow the flexible port seal 10 to be more easily compressed prior to insertion within an incision. Furthermore, these differences in lengths may allow the flexible port seal 10 to accommodate different types of surgical instrumentation, different surgical procedures, etc. As best shown in FIG. 2, a central support plate or disk 20 may be provided to support throughports 14, 16, and 18 within outer tissue seal 12.

With reference to FIG. 3, as shown, surgical instrumentation, such as, for example, conventional cannulas 82, 84, and 86 may be inserted through throughports 14, 16, and 18 (see FIG. 1). Cannulas 82, 84, and 86 include respective housings 88, 90, and 92. Housings 88, 90, and 92 include respective access tubes 94, 96, and 98 extending distally from housings 88, 90, and 92. With reference to cannula 86, for example, housing 92 of cannula 86 may be provided with an insufflation port 100 which is connected to a source of insufflation fluid to insufflate the area and within the body beneath tissue T. Alternatively, the flexible port seal 10 may have additional tubes, ports or connections (not shown) that separately operate to connect to and provide insufflation fluid or to provide smoke evacuation if desired. Once the body has been properly insufflated, an organ may be operated upon to excise it from the surrounding tissue.

Specifically, access tube 98 is inserted through throughport 18. As illustrated, throughport 18 is provided with an instrument seal, such as, for example an hourglass seal, which forms a fluid tight seal around access tube 98 inserted therethrough. Alternatively, the cannula 86 may be selected so as to have a tight fit within the throughbore of the throughport 18, thereby eliminating the need to have an instrument seal within the throughbore of the throughport 18. Also, the cannula 86 may include any type of fixation element, e.g., external threads, ribs, locking mechanisms, etc., that help maintain the cannula in position and help maintain the seal between the surface of the cannula 86 and the inner surface of the through-port 18.

However, in the exemplary embodiments of the present disclosure, it is contemplated to replace the support plate or disk 20, described above with reference to FIG. 2, with a cap assembly for positioning one or more access channels within an access assembly. The cap assembly may allow for a surgeon to selectively adjust the number of channels to be accessed, while performing a surgical procedure.

Figure 4A:
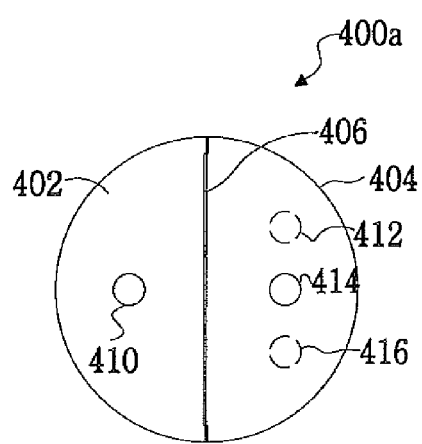
FIG. 4A is a top view of a cap assembly, according to an aspect of the present disclosure, where two channels are visible or accessible by a surgeon.
Figure 4B:
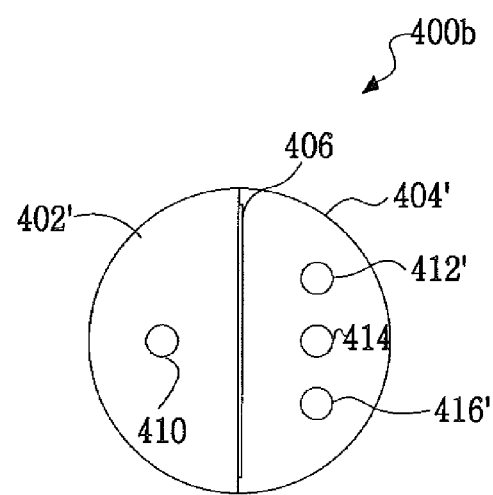
FIG. 4B is a top view of the cap assembly of FIG. 4A, according to an aspect of the present disclosure, where the foldable cap has been folded such that four channels are visible or accessible by the surgeon.

With reference to FIG. 4A, a top view of a cap assembly, according to an aspect of the present disclosure, where two channels are visible or accessible to a surgeon is presented. With reference to FIG. 4B, a top view of the cap assembly of FIG. 4A, according to an aspect of the present disclosure, where the foldable cap has been folded such that four channels are visible or accessible to a surgeon is presented.

Figure 5A:
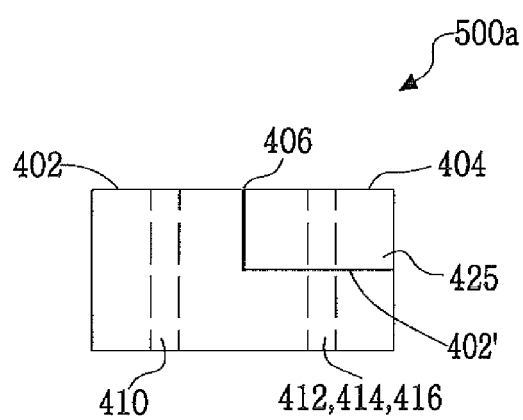
FIG. 5A is a side view of the foldable cap of FIG. 4A, according to an aspect of the present disclosure, depicting the foldable cap in a first configuration.
Figure 5B:
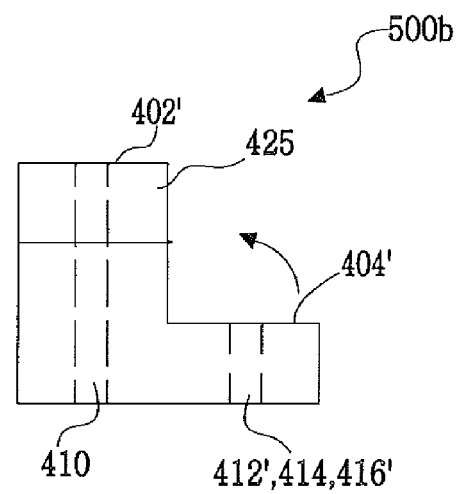
FIG. 5B is a side view of the foldable cap of FIG. 4B, according to an aspect of the present disclosure, depicting the foldable cap in a second configuration.

With reference to FIG. 5A, a side view of the foldable cap of FIG. 4A, according to an aspect of the present disclosure, depicting the foldable cap in a first configuration is presented. With reference to FIG. 5B, a side view of the foldable cap of FIG. 4B, according to an aspect of the present disclosure, depicting the foldable cap in a second configuration is presented.

The top view 400a of cap assembly 500a includes a first portion 402 and a second portion 404. The first portion 402 is connected to the second portion 404 via a connecting mechanism 406. The connection mechanism 406 may be at least a hinge, bracket or joint (e.g., pivotably attachable mechanism). The first portion 402 allows a surgeon access to a first channel 410. The second portion 404 includes three channels. However, in a first configuration, as shown in FIG. 4A, only one of the three channels is visible or accessible by the surgeon. For example, channel 414 is visible or accessible, whereas channels 412 and 416 are not yet visible and not accessible (shown with phantom lines). Thus, in the first configuration of the cap assembly 500a, the surgeon has access to 2 channels (e.g., 410 and 414) to work with when performing a surgical procedure. If the surgeon requires more channels to perform the surgical procedure, the surgeon may flip the second portion 404 onto the first portion 402 in order to expose further channels, as described with reference to FIGS. 4B and 5B.

In FIG. 4B, in a second configuration, the surgeon flips a cap segment 425 (see FIGS. 5A, 5B) to expose the other two channels (e.g., channels 412' and 416'). For instance, the top view 400b of cap assembly 500b of FIGS. 4B, 5B depict a first portion 402' and a second portion 404'. The first portion 402' is connected to the second portion 404' via a connecting mechanism 406. The first portion 402' is the bottom side of the second portion 404 of FIG. 4A. The second portion 404' is the exposed layer or surface of the cap assembly 400a (see FIGS. 5A and 5B for flipping action), after cap segment 425 has been flipped.

Once the surgeon flips the second portion 404 onto the first portion 402, the first portion 402' still allows access to the surgical site via the first channel 410. However, in contrast to FIG. 4A, as shown in FIG. 4B, the second portion 404' now allows access to all three channels (e.g., 412', 414, 416'). Therefore, with a flip of a cap segment 425, the surgeon may increase the available channels for a surgical procedure from 2 channels to 4 channels. This provides the surgeon with more flexibility before and during surgical procedures. The cap assembly 500a may be positioned within an access assembly, as described above with reference to FIGS. 1-3. However, it is contemplated that the cap assembly 500a may be an attachable component or unit that is removable attachable to existing access assemblies. Therefore, the foldable cap member is configured to fold in at least one direction to expose a second set of lumens extending the length of the tubular member of the access assembly.

With reference to FIG. 6A, a top view of a cap assembly, according to an aspect of the present disclosure, where two channels are visible or accessible to the surgeon is presented. With reference to FIG. 6B, a top view of the cap assembly of FIG. 6A, according to an aspect of the present disclosure, where the foldable cap has been folded such that three channels are visible or accessible to the surgeon is presented.

With reference to FIG. 7A, a side view of the foldable cap of FIG. 6B, according to an aspect of the present disclosure, depicting the foldable cap in a second configuration is presented. With reference to FIG. 7B, a side view of the foldable cap of FIG. 6B, according to an aspect of the present disclosure, depicting the foldable cap in a second configuration is presented.

The top view 600a of cap assembly 700a includes a first portion 602 and a second portion 604. The first portion 602 is connected to the second portion 604 via a connecting mechanism 606. The connection mechanism 606 may be at least a hinge, bracket or joint (e.g., pivotably attachable mechanism). The first portion 602 allows a surgeon access to a first channel 610. The second portion 604 includes two channels. However, in a first configuration, as shown in FIG. 6A, only one of the two channels is visible or accessible by the surgeon. For example, channel 616 is visible or accessible, whereas channel 612 is not yet visible and not accessible (shown with phantom lines). Thus, in the first configuration of the cap assembly 700a, the surgeon has access to 2 channels (e.g., 610 and 616) to work with when performing a surgical procedure. If the surgeon requires more channels to perform the surgical procedure, the surgeon may flip the second portion 604 onto the first portion 602 in order to expose further channels, as described with reference to FIGS. 6B and 7B.

In FIG. 7B, in a second configuration, the surgeon flips a cap segment 625 (see FIGS. 6A, 6B) to expose another channel (e.g., channel 612'). For instance, the top view 600b of cap assembly 700b of FIGS. 6B, 7B depict a first portion 602' and a second portion 604'. The first portion 602' is connected to the second portion 604' via a connecting mechanism 606. The first portion 602' is the bottom side of the second portion 604 of FIG. 6A. The second portion 604' is the exposed layer or surface of the cap assembly 600a (see FIGS. 7A and 7B for flipping action), after cap segment 625 has been flipped.

Once the surgeon flips the second portion 604 onto the first portion 602, the first portion 602' still allows access to the surgical site via the first channel 610. However, in contrast to FIG. 6A, as shown in FIG. 6B, the second portion 604' now allows access to both channels (e.g., 612', 616). Therefore, with a flip of a cap segment 625, the surgeon may increase the available channels for a surgical procedure from 2 channels to 3 channels. This provides the surgeon with more flexibility before and during surgical procedures. The cap assembly 700a may be positioned within an access assembly, as described above with reference to FIGS. 1-3. However, it is contemplated that the cap assembly 700a may be an attachable component or unit that is removably attachable to existing access assemblies. Therefore, the foldable cap member is configured to fold in at least one direction to expose a second set of lumens extending the length of the tubular member of the access assembly.

It is noted that FIGS. 4A-7B are merely exemplary. In FIGS. 4A-7B, the foldable cap member included two equally sized portions pivotally attached to each other. However, one skilled in the art may contemplate using a plurality of different cap assembly mechanisms in a number of different configurations to aid access to a number of different channels or lumens. Thus, it is contemplated that any number of initial channels may be initially exposed and that any number of subsequent channels may be subsequently revealed. It is contemplated that the cap assembly is split into more than 2 portions (as described with reference to FIGS. 8A-9B below).

Additionally, it is contemplated that the first portion may snap fit onto the second portion. It is contemplated that the first portion is a different size than the second portion. Moreover, the first set of lumens (initially exposed) may be configured to be a first size and the second set of lumens (subsequently revealed) may be configured to be a second size, the first and second sizes being different from each other. The second set of lumens may be configured to act as smoke vents for enabling smoke evacuation from a surgical site or may be configured to receive additional surgical instruments therethrough.

With reference to FIG. 8A, a top view of a cap assembly, according to an aspect of the present disclosure, where four channels are visible or accessible to the surgeon is presented. With reference to FIG. 8B, a top view of the cap assembly of FIG. 8A, according to an aspect of the present disclosure, where the foldable cap has been folded such that six channels are visible or accessible to the surgeon is presented.

With reference to FIG. 9A, a side view of the foldable cap of FIG. 8A, according to an aspect of the present disclosure, depicting the foldable cap in a first configuration is presented. With reference to FIG. 9B, a side view of the foldable cap of FIG. 8B, according to an aspect of the present disclosure, depicting the foldable cap in a second configuration is presented.

The top view 800a of cap assembly 900a includes a first portion 802, a second portion 804, a third portion 806, and a fourth portion 808. The first, second, third, and fourth portions 802, 804, 806, 808 are connected to each other via connecting mechanisms 810, 812. The connection mechanisms 810, 812 may be at least a hinge, bracket or joint (or pivotally attached members). In a first configuration, the first portion 802 allows the surgeon access to a first channel 820, the second portion 804 allows access to a second channel 824, the third portion 806 allows access to a third channel 828, and the fourth portion 808 allows access to a fourth channel 830. Thus, in the first configuration, as shown in FIG. 8A, four channels are visible or accessible by the surgeon. For example, channels 820, 824, 828, 830 are visible or accessible, whereas channels 822, 826 are not yet visible and not accessible (shown with phantom lines). Thus, in the first configuration of the cap assembly 800a, the surgeon has access to 4 channels (e.g., 820, 824, 828, 830) to work with when performing a surgical procedure. The channels 820, 824, 828, 830 are located at predetermined areas on portions 802, 804, 806, 808.

If the surgeon requires to access different organs via a single incision to perform the surgical procedure, the surgeon may flip the second portion 804 onto the first portion 802 and may also flip the third portion 806 onto the fourth portion 808 in order to expose additional channels that may be more convenient to access other organs during surgery, as described with reference to FIGS. 8B and 9B.

In FIG. 8B, in a second configuration, the surgeon flips cap segments 825 (see FIGS. 9A, 9B) to expose the other two channels (e.g., channels 822' and 826'). Once the surgeon flips the second portion 804 onto the first portion 802, and the third portion 806 onto the fourth portion 808, the first portion 802 still allows access to the surgical site via the first channel 820. However, in contrast to FIG. 8A, as shown in FIG. 8B, the first portion 802 also allows access to a new channel (e.g., 822'). Therefore, with a flip of a cap segment 825, the surgeon may increase the available channels for a surgical procedure from 1 channel to 2 channels in the first portion 802. Additionally, once the surgeon flips the third portion 806 onto the fourth portion 808, the third portion 806 still allows access to the surgical site via the third channel 828. However, in contrast to FIG. 8A, as shown in FIG. 8B, the third portion 806 also allows access to a new channel (e.g., 826'). Therefore, with a flip of a cap segment 825, the surgeon may increase the available channels for a surgical procedure from 1 channel to 2 channels in the third portion 806. As a result, the surgeon may flip two cap segments 825 in order to increase the number of channels from 4 to 6.

Once again, one skilled in the art may contemplate using a plurality of different cap assembly mechanisms in a number of different configurations to aid access to a number of different channels or lumens. Thus, it is contemplated that any number of initial channels may be initially exposed and that any number of subsequent channels may be subsequently revealed. It is contemplated that the cap assembly is split into a plurality of portions having a plurality of cap segments to be flipped.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of presently disclosed embodiments. Thus the scope of the embodiments should be determined by the appended claims and their legal equivalents, rather than by the examples given.

Persons skilled in the art will understand that the devices and methods specifically described herein and illustrated in the accompanying drawings are non-limiting exemplary embodiments. The features illustrated or described in connection with one exemplary embodiment may be combined with the features of other embodiments. Such modifications and variations are intended to be included within the scope of the present disclosure. As well, one skilled in the art will appreciate further features and advantages of the present disclosure based on the above-described embodiments. Accordingly, the present disclosure is not to be limited by what has been particularly shown and described, except as indicated by the appended claims.

The invention claimed is:

1. An access assembly comprising:
 a tubular member defining a longitudinal axis, the tubular member having a proximal end and a distal end, the proximal end in mechanical cooperation with a foldable cap member having a first set of lumens extending from the proximal end to the distal end of the tubular member, the tubular member configured to be tapered in a first position to facilitate insertion through tissue, the tubular member configured to define a substantially hour-glass shape in a second position, the foldable cap member having a connecting mechanism transverse to the longitudinal axis;
 a first ring secured at the proximal end of the tubular member; and
 a second ring secured at the distal end of the tubular member;
 wherein the foldable cap member is configured to fold in at least one direction to expose a second set of lumens extending a length of the tubular member.

2. The access assembly according to claim 1, wherein the first ring is configured to be received external of the tissue.

3. The access assembly according to claim 1, wherein the second ring is configured to be received within a body cavity.

4. The access assembly according to claim 1, wherein the foldable cap member includes two equally sized portions pivotably attached to each other.

5. The access assembly according to claim 4, wherein a first portion of the two equally sized portions is configured to snap fit over a second portion of the two equally sized portions to expose the second set of lumens.

6. The access assembly according to claim 1, wherein the foldable cap member includes a plurality of segments pivotably attached to each other.

7. The access assembly according to claim 1, wherein the foldable cap member includes a first portion and a second portion coupled to each other via the connecting mechanism, the first portion configured to fold onto the second portion to align the first and second set of lumens.

8. A method comprising:
   accessing a body cavity by:
      providing a tubular member defining a longitudinal axis, the tubular member having a proximal end and a distal end, the proximal end in mechanical cooperation with a foldable cap member having a first set of lumens extending from the proximal end to the distal end of the tubular member, the foldable cap member having a connecting mechanism transverse to the longitudinal axis;
      securing a first ring at the proximal end of the tubular member;
      securing a second ring at the distal end of the tubular member; and
      folding the foldable cap member over a portion of the foldable cap member to expose a second set of lumens extending a length of the tubular member.

9. The method according to claim 8, wherein the foldable cap member includes two equally sized portions pivotably attached to each other.

10. The method according to claim 9, wherein a first portion of the two equally sized portions is configured to snap fit over a second portion of the two equally sized portions to expose the second set of lumens.

11. The method according to claim 8, wherein the foldable cap member includes a first portion and a second portion coupled to each other via the connecting mechanism, the first portion configured to fold onto the second portion to align the first and second set of lumens.

* * * * *